(12) United States Patent
Nakaya

(10) Patent No.: US 8,152,725 B2
(45) Date of Patent: Apr. 10, 2012

(54) ULTRASONIC DIAGNOSTIC APPARATUS AND IMAGE DISPLAY METHOD THEREOF

(75) Inventor: Shigemitsu Nakaya, Otawara (JP)

(73) Assignees: Kabushiki Kaisha Toshiba, Tokyo (JP); Toshiba Medical Systems Corporation, Otawara-shi (JP)

(*) Notice: Subject to any disclaimer, the term of this patent is extended or adjusted under 35 U.S.C. 154(b) by 949 days.

(21) Appl. No.: 12/106,526

(22) Filed: Apr. 21, 2008

(65) Prior Publication Data

US 2008/0269605 A1 Oct. 30, 2008

(30) Foreign Application Priority Data

Apr. 25, 2007 (JP) ................. 2007-116123

(51) Int. Cl.
*A61B 8/00* (2006.01)
(52) U.S. Cl. ...................... 600/443; 600/438
(58) Field of Classification Search .......... 600/437, 600/438, 443
See application file for complete search history.

(56) References Cited

U.S. PATENT DOCUMENTS

| | | | |
|---|---|---|---|
| 6,500,119 B1 * | 12/2002 | West et al. | 600/437 |
| 6,514,204 B2 * | 2/2003 | Alam et al. | 600/442 |
| 6,558,324 B1 * | 5/2003 | Von Behren et al. | 600/440 |
| 6,638,221 B2 | 10/2003 | Abe et al. | |
| 7,048,691 B2 * | 5/2006 | Miele et al. | 600/504 |
| 7,223,241 B2 * | 5/2007 | Radulescu | 600/443 |
| 2002/0065461 A1 * | 5/2002 | Cosman | 600/426 |
| 2007/0282202 A1 * | 12/2007 | Maurice et al. | 600/438 |
| 2008/0269606 A1 * | 10/2008 | Matsumura | 600/438 |

FOREIGN PATENT DOCUMENTS

| | | |
|---|---|---|
| JP | 2003-175041 | 6/2003 |
| JP | 2003-225239 | 8/2003 |
| WO | 2005/120358 A1 | 12/2005 |

* cited by examiner

*Primary Examiner* — Jacqueline Cheng
(74) *Attorney, Agent, or Firm* — Oblon, Spivak, McClelland, Maier & Neustadt, L.L.P.

(57) ABSTRACT

A generation unit generates data of a plurality of images whose scan time is different on the basis of an output of the probe. A calculation unit calculates a plurality of index values related to pressure of the probe against the tested body on the basis of a physical quantity changing with the strength of the pressure. A specifying unit specifies a first image, which corresponds to a first index value of the plurality of calculated index values, and a second image, which corresponds to a second index value, among the plurality of generated images. A display unit displays the specified first and second images side by side.

24 Claims, 11 Drawing Sheets

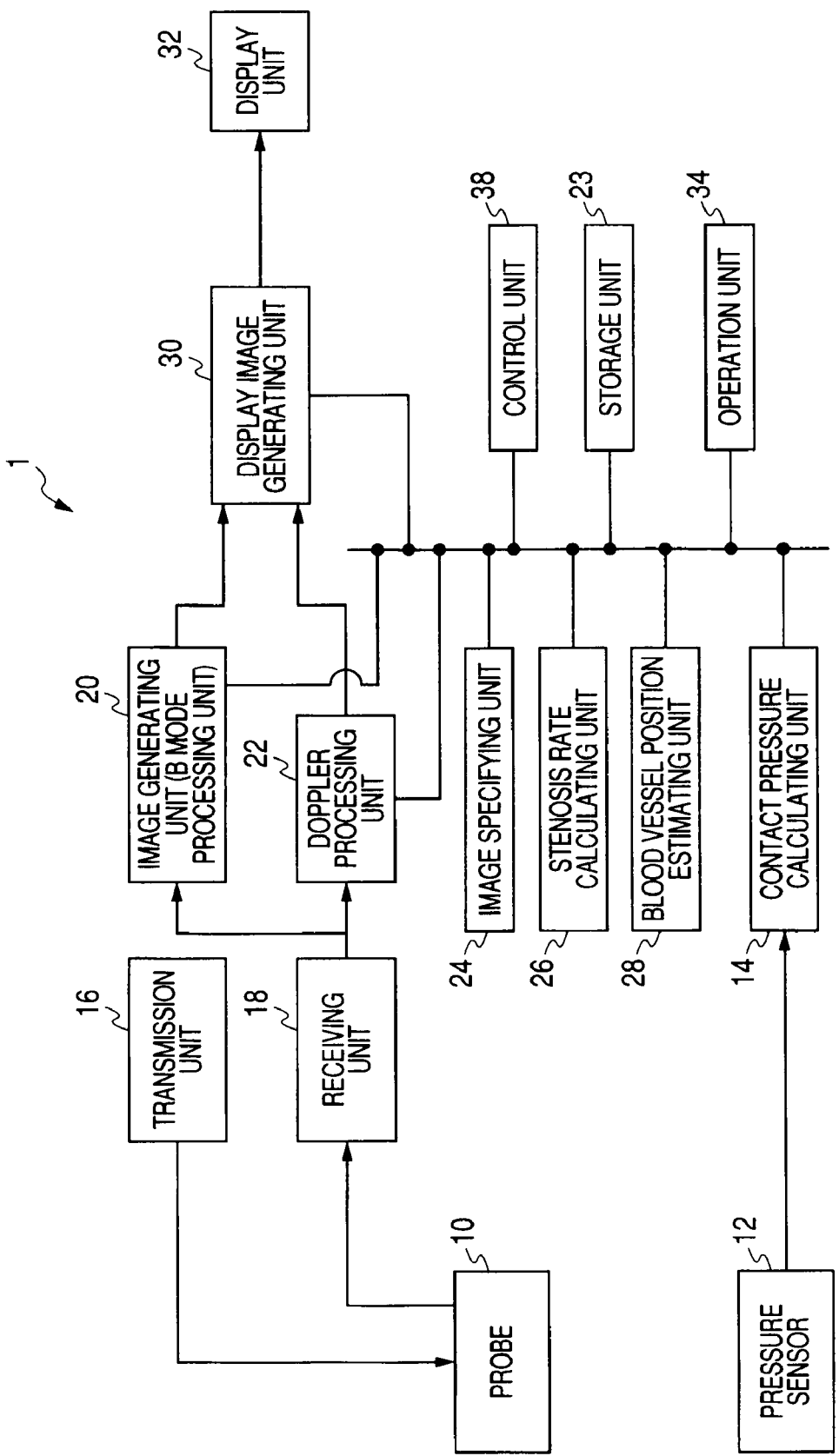

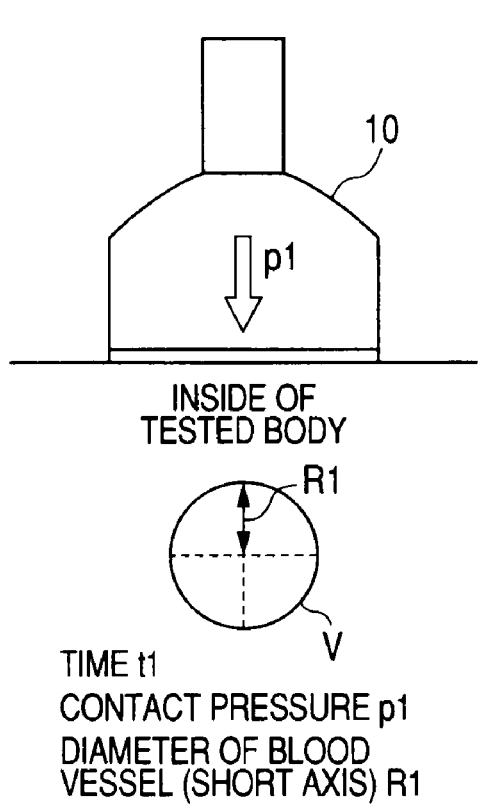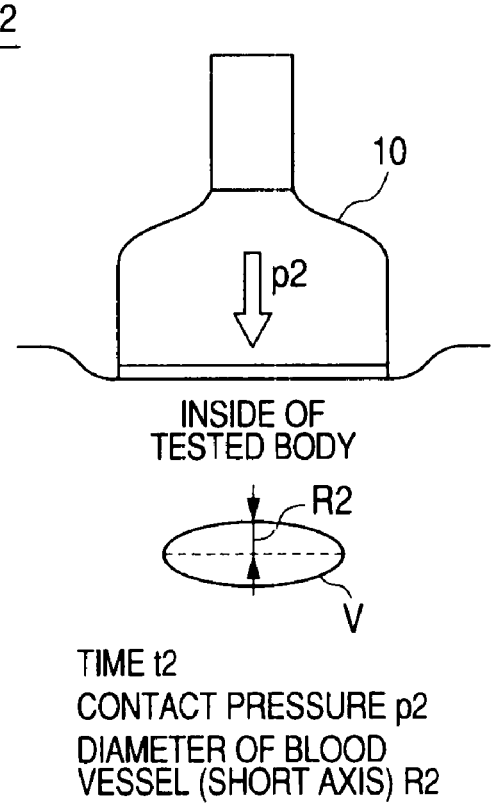

VOLUME DATA

3D IMAGE REGARDING SECTION S

ULTRASONIC DIAGNOSTIC APPARATUS AND IMAGE DISPLAY METHOD THEREOF

CROSS-REFERENCE TO RELATED APPLICATIONS

This application is based upon and claims the benefit of priority from prior Japanese Patent Application No. 2007-116123, filed Apr. 25, 2007, the entire contents of which are incorporated herein by reference.

BACKGROUND OF THE INVENTION

1. Field of the Invention

The present invention relates to an ultrasonic diagnostic apparatus that scans a tested body pressed by a probe and an image display method thereof.

2. Description of the Related Art

In recent years, a diagnosis (hereinafter, referred to as a blood vessel echo) of a blood vessel using an ultrasonic wave is being widely performed. In the blood vessel echo, the existence of an intravascular thrombus or vascular stenosis and occlusion are diagnosed for various parts, such as a carotid artery, a main artery, a coronary artery, a peripheral artery, and a peripheral vein.

There is a deep vein thrombosis (hereinafter, referred to as a 'DVT') as a disease related to a thrombus. The DVT is a disease causing a thrombus to be formed in a deep vein. Most of the thrombi are generated in a leg. The formed thrombus may peel and fall from a blood vessel wall. Such a thrombus that peels and fall is called an embolus. The blood of a leg vein passes through the heart and flows to a lung. For this reason, an embolus generated in the leg vein may be blocked in the artery of the lung after passing through the heart, which causes pulmonary embolism. That is, the thrombus formed in the leg vein may serve as a source of embolus of pulmonary embolism.

In order to prove the existence of a thrombus, the thrombus may be visualized on an ultrasonic image or disappearance of a Doppler signal related to a venous blood flow may be checked. In addition, the venous blood pressure of a blood vessel of a vein (for example, a femoral vein or a popliteal vein) near a body surface is low if the blood vessel is not occluded. Accordingly, the blood vessel deforms easily when the body surface is pressed with a probe. On the other hand, in the case when the blood vessel is not occluded, the blood vessel does not deform even if the body surface is pressed. Therefore, the existence of a thrombus can be determined by checking whether or not a blood vessel is deformed by pressure.

In recent years, the following techniques useful for determining whether or not a blood vessel deforms when pressing a tested body are disclosed.

1. A blood vessel moves when a tested body is pressed. A technique of tracing a part moving on an ultrasonic image, which is useful in such a case (for example, refer to JP-A-2003-175041).

2. A probe having a pressure sensor provided on a contact surface being in contact with a tested body, which is useful in the case of measuring a pressure value when pressing the tested body (for example, refer to JP-A-2003-225239).

SUMMARY OF THE INVENTION

However, there are the following problems in observing deformation of a blood vessel occurring when pressing a probe against a body surface.

(1) It is difficult to observe deformation of a blood vessel caused by pressure since an ultrasonic image is generated and displayed continuously in real time.

(2) It may be difficult to observe deformation of a blood vessel caused by pressure in the case when the blood vessel moves or a scan section shifts by pressure using a probe.

(3) The position of a vein may be missing in the case when the vein completely disappears from an ultrasonic image due to pressure using a probe.

It is an object of the invention to provide an ultrasonic diagnostic apparatus capable of easily determining deformation of a specifying unit of a tested body, which occurs when being pressed, and an image display method thereof.

According to a first aspect of the invention, an ultrasonic diagnostic apparatus that repeatedly scans a tested body with an ultrasonic wave by using a probe includes: a generation unit that generates data of a plurality of images whose scan time is different on the basis of an output of the probe; a first calculation unit that calculates a plurality of index values related to pressure of the probe against the tested body on the basis of a physical quantity changing with the strength of the pressure; a specifying unit that specifies a first image, which corresponds to a first index value of the plurality of calculated index values, and a second image, which corresponds to a second index value, among the plurality of generated images; and a display unit that displays the specified first and second images side by side.

According to a second aspect of the invention, an image display method of an ultrasonic diagnostic apparatus that repeatedly scans a tested body with an ultrasonic wave by using a probe includes: generating data of a plurality of images whose scan time is different on the basis of an output of the probe; calculating a plurality of index values related to pressure of the probe against the tested body on the basis of a physical quantity changing with the strength of the pressure; specifying a first image, which corresponds to a first index value of the plurality of calculated index values, and a second image, which corresponds to a second index value, among the plurality of generated images; and displaying the specified first and second images side by side.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 1 is a view illustrating the configuration of an ultrasonic diagnostic apparatus according to a first embodiment of the invention;

FIGS. 2A and 2B are views for explaining a stenosis rate calculated by a stenosis rate calculating unit shown in FIG. 1;

DESCRIPTION OF THE PREFERRED EMBODIMENTS

Figure 3:
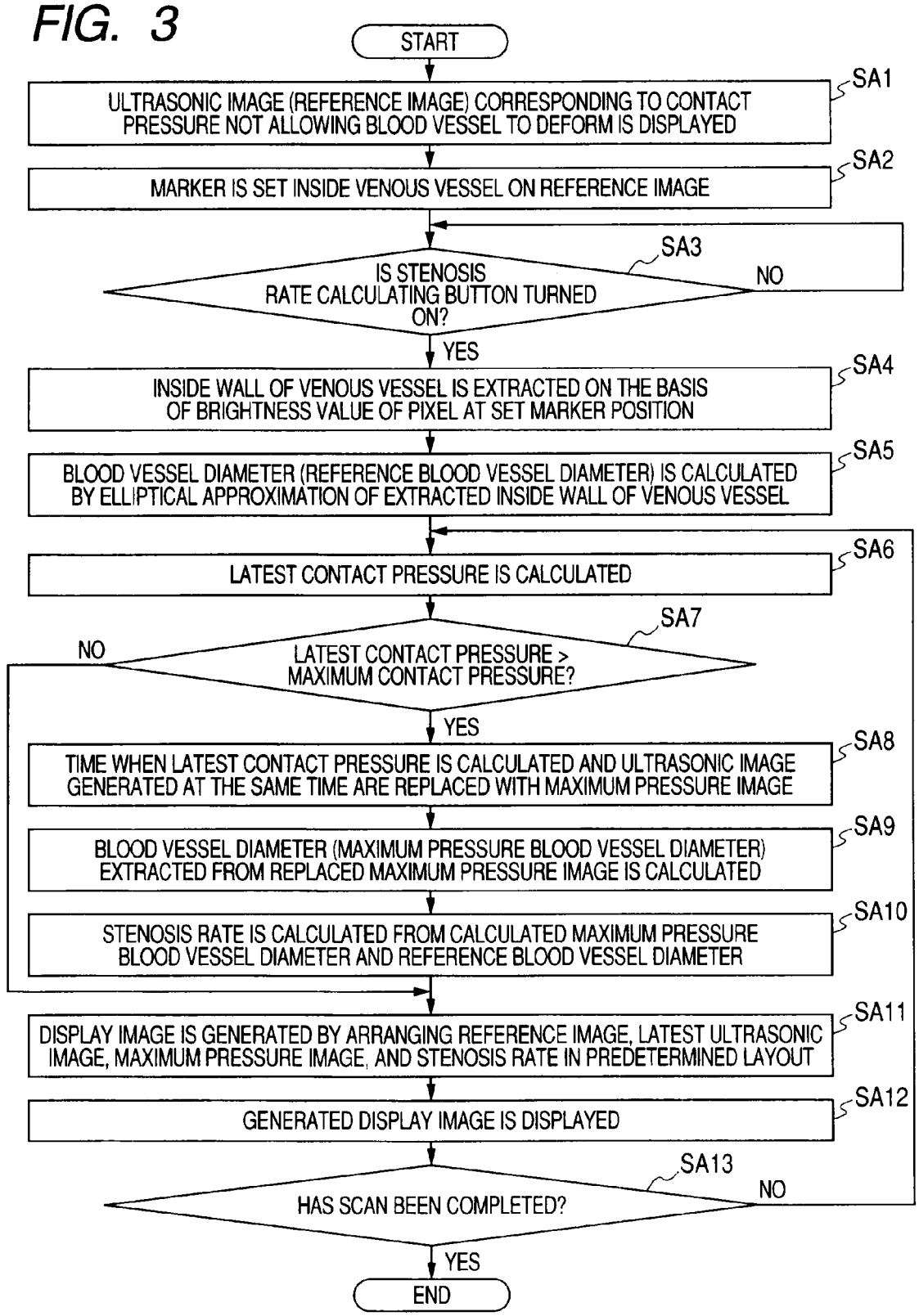
FIG. 3 is a view illustrating the flow of processing, which is performed under the control of a control unit shown in FIG. 1, in the first embodiment.

Hereinafter, ultrasonic diagnostic apparatuses according to the first and second embodiments of the invention will be described with reference to the accompanying drawings. The ultrasonic diagnostic apparatus according to each of the first and second embodiments generates data of an ultrasonic image repeatedly while pressing a tested body with a probe. An operator observes deformation of a venous vessel visualized on the generated ultrasonic image. At this time, in order to make it easy to observe deformation of a venous vessel, the ultrasonic diagnostic apparatus according to each of the first and second embodiments specifies a set of ultrasonic images, in which deformation is easily observed, on the basis of various kinds of index values changing with pressure of a probe against a tested body and displays the set of specified ultrasonic images side by side. Hereinafter, these index values will be referred to as pressure index values.

First Embodiment

In a first embodiment, a pressure index value refers to a contact pressure between a probe and a tested body, which is caused by pressing the tested body with the probe.

FIG. 1 is a view illustrating the configuration of an ultrasonic diagnostic apparatus 1 according to the first embodiment. As shown in the FIG. 1, the ultrasonic diagnostic apparatus 1 includes a probe 10, a pressure sensor 12, a contact pressure calculating unit 14, a transmission unit 16, a receiving unit 18, an image generating unit (B-mode processing unit) 20, a Doppler processing unit 22, a storage unit 23, an image specifying unit 24, a stenosis rate calculating unit 26, a blood vessel position estimating unit 28, a display image generating unit 30, a display unit 32, an operation unit 34, and a control unit 38. Hereinafter, each of the constituent components will be described.

The probe 10 has a vibrator array in which a plurality of vibrators for converting electric signals into ultrasonic waves are arrayed. Transmission and reception of a supersonic wave with respect to a tested body are performed through the vibrator array. In addition, the probe 10 has a contact surface being in contact with a tested body. The contact surface is brought into contact with the tested body and is pressed by an operator.

The pressure sensor 12 is connected to the contact surface of the probe 10 and detects a contact pressure between the probe 10 and the tested body. The pressure sensor 12 is a known technique disclosed in JP-A-2003-225239, for example. The pressure sensor 12 has a mechanism that generates the strain by contact pressure with a tested body and converts the strain into an electric signal (physical quantity) corresponding to the intensity of the strain. The generated electric signal is transmitted to the contact pressure calculating unit 14 by the pressure sensor 12.

The contact pressure calculating unit 14 calculates a contact pressure based on the transmitted electric signal. The calculated contact pressure is stored in the storage unit 23 so as to relate to a calculation time.

The transmission unit 16 has a rate pulse generating circuit, a delay circuit, and a driving pulse generating circuit, all of which are not shown in the drawing.

The rate pulse generating circuit repeatedly generates a rate pulse in a predetermined rate frequency fr Hz (period; 1/fr second). The delay circuit makes ultrasonic waves converge in the beam shape for every channel and gives a delay time, which is required for determining transmission directivity, to each rate pulse. The driving pulse generating circuit generates a driving pulse at timing based on each delayed rate pulse and applies the generated driving pulse to the probe 10.

The receiving unit 18 has an amplifying circuit, an A/D converter, and an adder, all of which are not shown in the drawing. The amplifying circuit amplifies an echo signal (physical quantity) from the tested body, which is an output of the probe 10, for every channel. The A/D converter converts the amplified echo signal from an analog signal to a digital signal. The delay circuit makes the echo signal converted into the digital signal converge in the beam shape and gives a delay time, which is required for sequentially changing receiving directivity, to each echo signal. The adder adds the echo signals to which the delay time is applied.

The image generating unit 20 receives supply of the echo signal from the receiving unit 18, performs logarithmic amplification of the echo signal, performs envelope detection processing for the logarithmically amplified echo signal, and generates brightness data in which the signal strength is expressed as the brightness. The image generating unit 20 generates an ultrasonic image (B-mode image) related to a two-dimensional tomographic plane on the basis of the generated brightness data. The ultrasonic image is stored in the storage unit 23 so as to be related to the generation time.

The Doppler processing unit 22 receives supply of the echo signal from the receiving unit 18 and calculates a signal (hereinafter, referred to as a Doppler signal) that is shifted by the Doppler shift frequency by performing frequency analysis of the echo signal. The Doppler processing unit 22 calculates the movement speed of a blood flow and the like on the basis of the calculated Doppler signal. Since the blood flow speed of an artery is faster than that of a vein, the artery and the vein can be distinguished from each other by using the Doppler signal. In addition, the Doppler processing unit 22 generates data of a Doppler image showing two-dimensional distribution on a predetermined section, such as a speed, variance, or power of a blood flow or the like.

The storage unit 23 stores data of an ultrasonic image and generation time thereof so as to be related to each other. The storage unit 23 stores data of a contact pressure and generation time thereof so as to be related to each other. In addition, the storage unit 23 stores a contact pressure and an ultrasonic image, which is generated at approximately the same time as when the contact pressure is calculated, so as to be related to each other. In addition, the storage unit 23 stores various kinds of data of a display image and a stenosis rate, for example, which will be described later.

The image specifying unit 24 specifies a specific contact pressure from the contact pressure repeatedly calculated and specifies an ultrasonic image related to the specific contact pressure that is specified. For example, the image specifying unit 24 specifies a maximum contact pressure from the contact pressure repeatedly calculated and specifies an ultrasonic image related to the specified maximum contact pressure.

The stenosis rate calculating unit 26 has an extraction function, a function for calculating a blood vessel diameter, and a function for calculating a stenosis rate. Hereinafter, each of the functions will be described.

As for the extraction function, the stenosis rate calculating unit 26 extracts an inner wall of a venous vessel on the basis of the similarity of a brightness value inside a venous vessel visualized on the ultrasonic image.

As for the function for calculating a blood vessel diameter, the stenosis rate calculating unit 26 performs elliptical approximation of the inner wall of the extracted venous vessel. Then, the stenosis rate calculating unit 26 calculates the length of a radius of a short axis of the ellipse as the blood vessel diameter.

As for the function for calculating a stenosis rate, the stenosis rate calculating unit 26 calculates an index value, which indicates the degree of deformation of two blood vessels, from two blood vessel diameters related to two ultrasonic images. The index value indicating the degree of deformation is a stenosis rate of a blood vessel, for example.

FIGS. 2A and 2B are views for explaining a stenosis rate and illustrate a blood vessel diameter changing with the strength of a contact pressure. It is assumed that a contact pressure p1 at time t1 is smaller than a contact pressure p2 at time t2 (p1<p2). The contact pressure p1 is a contact pressure that does not allow a blood vessel V to deform. The contact pressure p1 is assumed to be called a reference contact pressure p1. An ultrasonic image generated at approximately the same time as when a tested body is pressed with the reference contact pressure p1 is called a reference image. The blood vessel diameter (hereinafter, referred to as a reference blood vessel diameter) of the blood vessel V visualized on the reference image is set to R1. The blood vessel diameter of the blood vessel V visualized on an ultrasonic image generated at approximately the same time as when the tested body is pressed with the contact pressure p2 is set to R2. The stenosis rate is expressed as (R2/R1)×100.

A stenosis rate is 0% when the blood vessel V disappears (R2=0) and is 100% when the blood vessel V does not deform at all (R1=R2).

When a venous vessel disappears from an ultrasonic image by pressing a tested body (blood vessel diameter=0), the blood vessel position estimating unit 28 calculates a vector (distance, direction, and orientation) between a blood vessel in an ultrasonic image generated immediately before a blood vessel disappears and a specifying unit, in which the relative positional relationship with the blood vessel does not change, and estimates the position of a blood vessel disappeared from the calculated vector. For example, the specifying unit is an artery or a muscular layer running side by side with a vein.

The display image generating unit 30 generates data of a display image in which deformation of a blood vessel can be easily viewed. Specifically, the display image generating unit 30 generates data of a display image by arranging an ultrasonic image, which corresponds to a contact pressure not allowing a blood vessel to deform, and an ultrasonic image, which corresponds to a maximum contact pressure, side by side. In addition, the display image generating unit 30 may arrange an ultrasonic image generated in real time side by side with the two ultrasonic images. In addition, the display image generating unit 30 may arrange the calculated stenosis rate or the calculated blood vessel side by side with an ultrasonic image. In addition, the display image generating unit 30 may arrange an arrow or the like in order to indicate and display the blood vessel position estimated by the blood vessel position estimating unit 28.

The display unit 32 displays a display image generated by the display image generating unit 30. Specifically, the display unit 32 displays an ultrasonic image, which corresponds to a contact pressure not allowing a blood vessel to deform, and an ultrasonic image, which corresponds to the maximum contact pressure, side by side. In addition, the display unit 32 performs motion display of an ultrasonic image generated in real time. In addition, the display unit 32 displays the calculated stenosis rate or the calculated blood vessel diameter side by side with an ultrasonic image. In addition, the display unit 32 arranges an arrow or the like in order to indicate and display the blood vessel position estimated by the blood vessel position estimating unit 28.

The operation unit 34 is an input device including a keyboard, various kinds of switches, a mouse, and the like. Specifically, the operation unit 34 includes a scan start button, a scan stop button, a stenosis rate calculating button, and the like.

The control unit 38 controls each constituent component in order to realize an operation as the ultrasonic diagnostic apparatus 1. Hereinafter, an example of processing in the first embodiment, which is performed under the control of the control unit 38, will be described. FIG. 3 is a view illustrating the flow of processing in the first embodiment.

[Step SA1]

First, an operator presses the probe 10 against a tested body with the reference contact pressure and presses the scan start button provided in the operation unit 34. When the scan start button is pressed, the control unit 38 generates a reference image by performing scan in a condition of the reference contact pressure and displays the generated reference image on the display unit 32. The contact pressure is detected by the pressure sensor 12 and is calculated by the contact pressure calculating unit 14.

[Step SA2]

Figure 4:
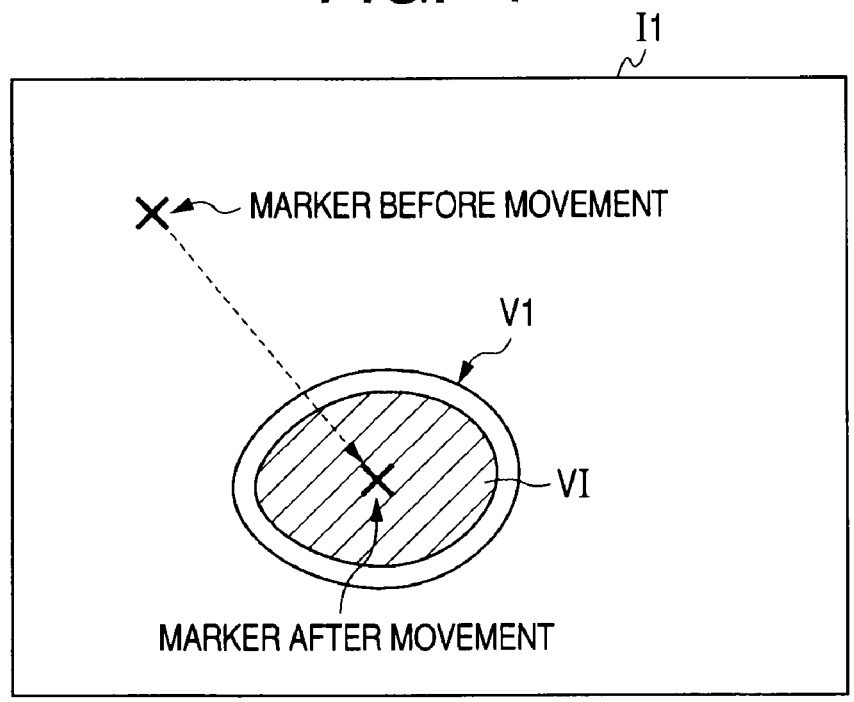
FIG. 4 is a view for explaining processing in step SA2 shown in FIG. 3.

The control unit 38 sets a marker inside a venous vessel on the reference image through the operation unit 34. FIG. 4 is a view for explaining processing in step SA2 and illustrates a reference image I1 displayed on the display unit 32. As shown in FIG. 4, the operator moves the marker, which is displayed on the reference image I1, to the inside VI of the venous vessel V1 through the operation unit 34.

[Step SA3]

The control unit 38 waits for the operator to request processing for calculating a stenosis rate.

The control unit 38 proceeds to step SA4 when the operator presses the stenosis rate calculating button provided in the operation unit 34.

[Step SA4]

The control unit 38 makes the stenosis rate calculating unit 26 perform extraction processing. In the extraction processing, the stenosis rate calculating unit 28 extracts an inner wall of the venous vessel on the basis of a pixel at the position of a marker after movement, that is, a brightness value of a pixel inside the venous vessel.

[Step SA5]

The control unit 38 makes the stenosis rate calculating unit 26 perform processing for calculating the blood vessel diameter. In the processing for calculating the blood vessel diameter, the stenosis rate calculating unit 26 performs elliptical approximation of the inner wall of the venous vessel extracted in step SA4 and calculates the reference blood vessel diameter.

[Step SA6]

Figure 5:
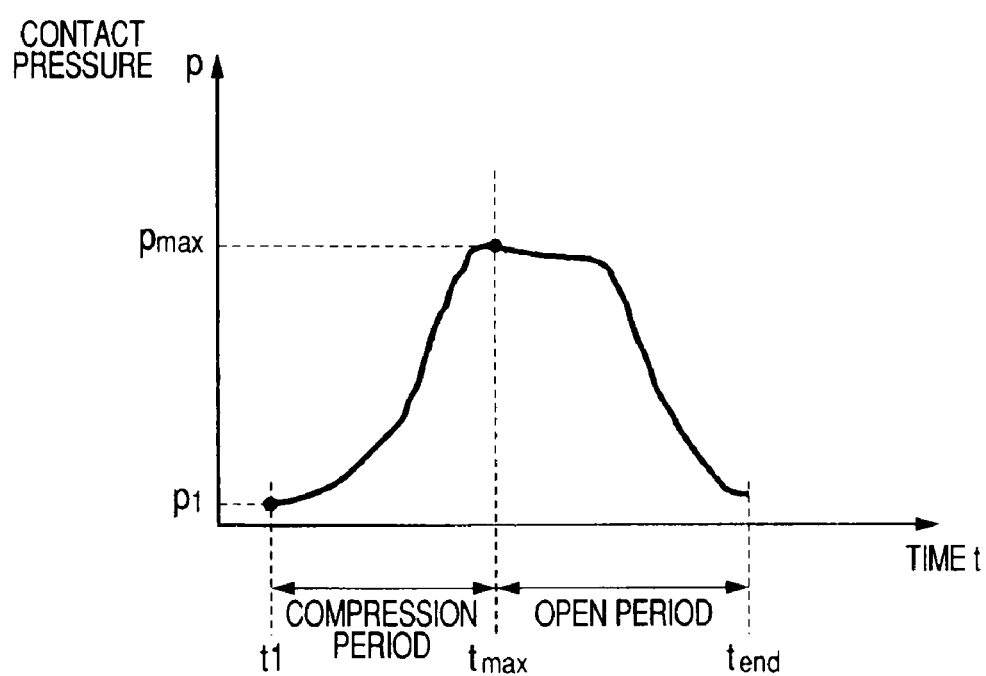
FIG. 5 is a view illustrating an example of the relationship between a contact pressure p and a time t in scan in the first embodiment.

When the reference blood vessel diameter is calculated in step SA5, the operator starts to press the tested body with the probe 10. While pressing the tested body, the control unit 38 scans the tested body through the probe 10 and generates data of an ultrasonic image in real time. In addition, a contact pressure is also calculated in real time. The calculated contact pressure changes according to the strength of the operator's pressure. FIG. 5 is a view illustrating an example of the relationship between a contact pressure p and a time t in scan. Time t1 is a pressure start time (time when a stenosis rate measurement switch is pressed by the operator), and the contact pressure p1 at that time is assumed to be a reference contact pressure. It is assumed that the contact pressure p increases by the operator when scan starts and reaches a true maximum contact pressure $p_{max}$ at a time $t_{max}$. The true maximum contact pressure $p_{max}$ is a largest contact pressure among contact pressures calculated in a period from the start of scan to the end of scan. A period for which the contact pressure increases is assumed to be a pressure period. After the time $t_{max}$, the contact pressure continues decreasing and the scan stop button is pressed by the operator at a time tend, and thus scan ends. A period for which the contact pressure decreases is assumed to be an open period.

Data of the newest ultrasonic image is generated and the newest contact pressure is calculated under the change of contact pressure shown in FIG. 5. The newest ultrasonic image generated is stored in the storage unit 23 so as to be related to the elapsed time from time t1, for example. In addition, the newest contact pressure calculated is also stored in the storage unit 23 so as to be related to the elapsed time from time t1.

[Step SA7]

When the newest contact pressure is calculated in step SA6, the control unit 38 makes the image specifying unit 24 perform image specifying processing. In the image specifying processing, the image specifying unit 24 compares the calculated newest contact pressure with a maximum contact pressure immediately before the newest contact pressure is calculated. When it is determined that the newest contact pressure is larger than the maximum contact pressure immediately before the newest contact pressure is calculated, the image specifying unit 24 proceeds to step SA8. When it is determined that the newest contact pressure is smaller than the maximum contact pressure immediately before the newest contact pressure is calculated, the image specifying unit 24 proceeds to step SA11. Since the newest contact pressure is larger than the maximum contact pressure immediately before the newest contact pressure is calculated in the pressure period of FIG. 5, the process proceeds from step SA7 to step SA8. Since the newest contact pressure is smaller than the maximum contact pressure immediately before the newest contact pressure is calculated in the open period of FIG. 5, the process proceeds from step SA7 to step SA11.

[Step SA8]

When it is determined that the newest contact pressure is larger than the maximum contact pressure immediately before the newest contact pressure is calculated in step SA7, the image specifying unit 24 sets the newest contact pressure to the maximum contact pressure. When the maximum contact pressure is set, the image specifying unit 24 specifies an ultrasonic image generated at approximately the same time as when the newest contact pressure is calculated. Then, the image specifying unit 24 replaces the specified ultrasonic image with a maximum pressure image. It is assumed that the maximum pressure image is updated each time during the pressure period.

[Step SA9]

When the maximum pressure image is updated in step SA8, the control unit 38 makes the stenosis rate calculating unit 26 perform processing for calculating the blood vessel diameter. In the processing for calculating the blood vessel diameter, the stenosis rate calculating unit 26 calculates the blood vessel diameter in the maximum pressure image updated in step SA8. In addition, in the case when the position of a venous vessel visualized on an ultrasonic image changes due to pressure, the stenosis rate calculating unit 26 traces the venous vessel and calculates the blood vessel diameter related to the maximum pressure image by using a known technique, for example, a technique disclosed in JP-A-2003-175041.

[Step SA10]

When the blood vessel diameter related to the maximum pressure image is calculated in step SA9, the control unit 38 makes the stenosis rate calculating unit 26 perform processing for calculating a stenosis rate. In the processing for calculating a stenosis rate, the stenosis rate calculating unit 26 calculates the stenosis rate on the basis of the reference blood vessel diameter calculated in step SA5 and the blood vessel diameter related to the maximum pressure image calculated in step SA9. As described above, the stenosis rate is calculated by (R2/R1)×100 assuming that a reference blood vessel diameter is R1 and a maximum pressure blood vessel diameter is R2.

[Step SA11]

When the stenosis rate is calculated in step SA10 or when it is determined that the newest contact pressure is smaller than the maximum contact pressure before the newest contact pressure is calculated in step SA7, the control unit 38 makes the display image generating unit 30 perform processing for generating a display image. In the processing for generating a display image, when the processing in step SA10 has been performed, the display image generating unit 30 generates data of a display image in which the reference image generated in step SA1, the newest ultrasonic image generated in step SA6, the maximum pressure image updated in step SA8, and the stenosis rate calculated in step SA10 are arranged in a predetermined layout. When the processing in step SA10 has not been performed, the display image generating unit 30 generates data of a display image in which the reference image generated in step SA1, the newest ultrasonic image generated in step SA6, a set maximum pressure image, and a set stenosis rate are arranged in a predetermined layout.

Figure 6:
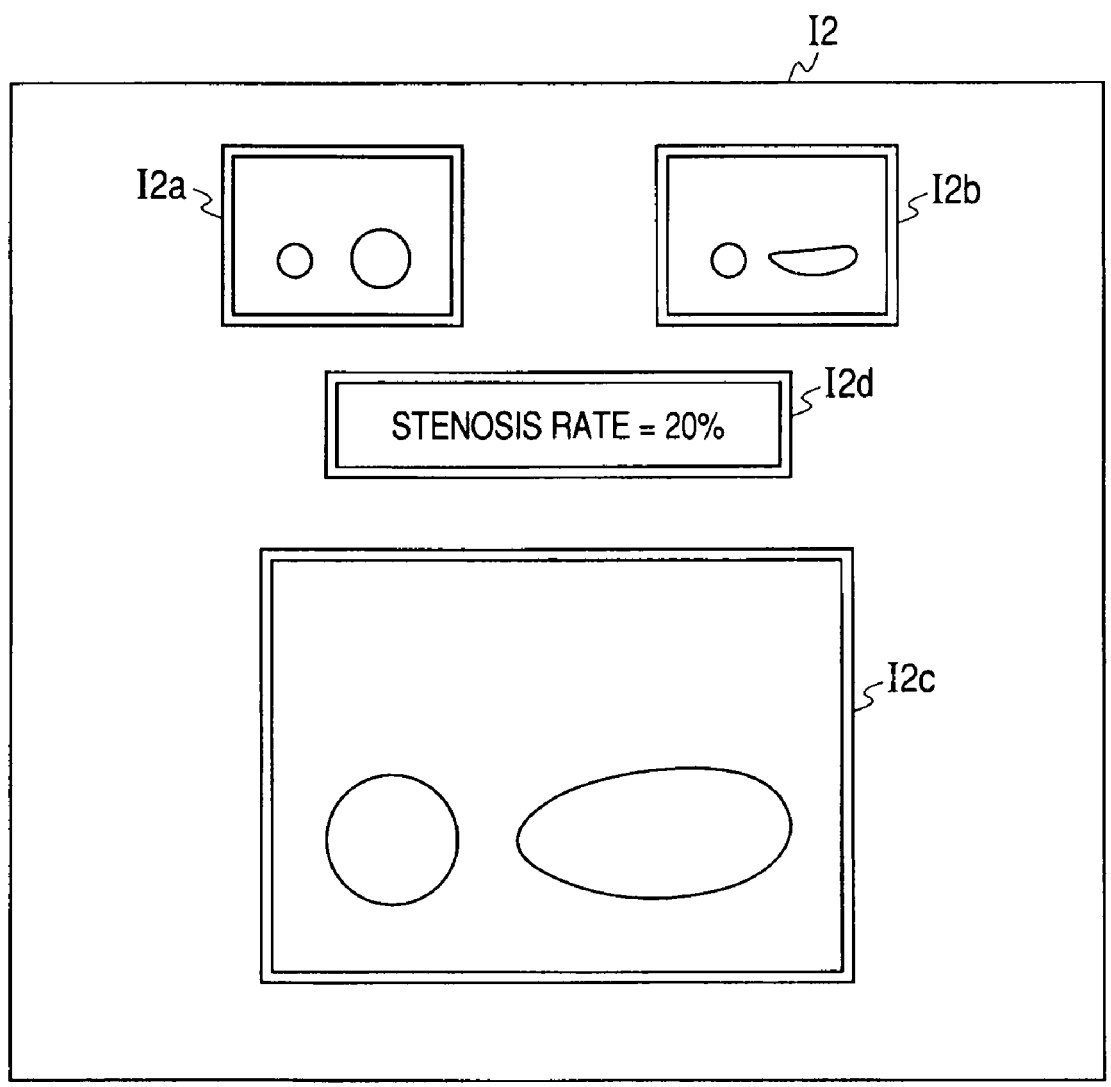
FIG. 6 is a view illustrating an example of a display image displayed by the display unit shown in FIG. 1.

FIG. 6 is a view illustrating an example of a display image 12 generated in step SA11. The display image 12 has a display region I2a of a reference image, a display region I2b of a maximum pressure image, a display region I2c of a newest ultrasonic image, and a stenosis rate display region I2d. In the display region I2a, the reference image generated in step SA1 is displayed. In the display region I2b, the newest maximum pressure image specified in step SA7 is displayed. In the display region I2c, the newest ultrasonic image generated in step SA6 is displayed. In the display region I2d, the stenosis rate calculated in step SA10 is displayed.

For example, in the pressure period shown in FIG. 5, ultrasonic images that are continuously generated in step SA6 during the pressure period are motion displayed in the display region I2b of the maximum pressure image and the display region I2c of the newest ultrasonic image. In the open period shown in FIG. 5, an ultrasonic image in the true maximum contact pressure $p_{max}$ is displayed in the display region I2b. In addition, the newest ultrasonic image that is generated in real time in step SA6 during the open period is motion displayed in the display region 12c.

In addition, the display image generating unit 30 may display a value of the blood vessel diameter of a blood vessel visualized on the reference image in the display region I2a of the reference image and may display a value of the blood vessel diameter of a blood vessel visualized on the maximum pressure image in the display region I2b of the maximum pressure image. In addition, while displaying the value of the blood vessel diameter, a stenosis rate and a comment corresponding to the stenosis rate may also be displayed on the stenosis rate display region I2d. For example, 'stenosis rate is 20%. There is a possibility of thrombus' may be displayed.

[Step SA12]

When a display image is generated in step SA11, the control unit 38 displays the display image on the display unit 32.

[Step SA13]

Steps SA6 to SA12 are repeated until the scan stop button provided in the operation unit 34 is pressed by the operator. The control unit 38 ends the scan when the scan stop button is pressed.

In addition, a change in contact pressure in the processing shown in FIG. 3 has changed as shown in FIG. 5. However, the change in contact pressure does not need to be limited thereto. For example, the contact pressure may be a contact pressure $p_{min}$ smaller than the contact pressure p1 after time t1. In this case, the image specifying unit 24 may perform subsequent processing in the same manner as the above method by setting the contact pressure $p_{min}$ as a reference contact pressure and an ultrasonic image corresponding to the contact pressure $p_{min}$ as a reference image.

Figure 7:
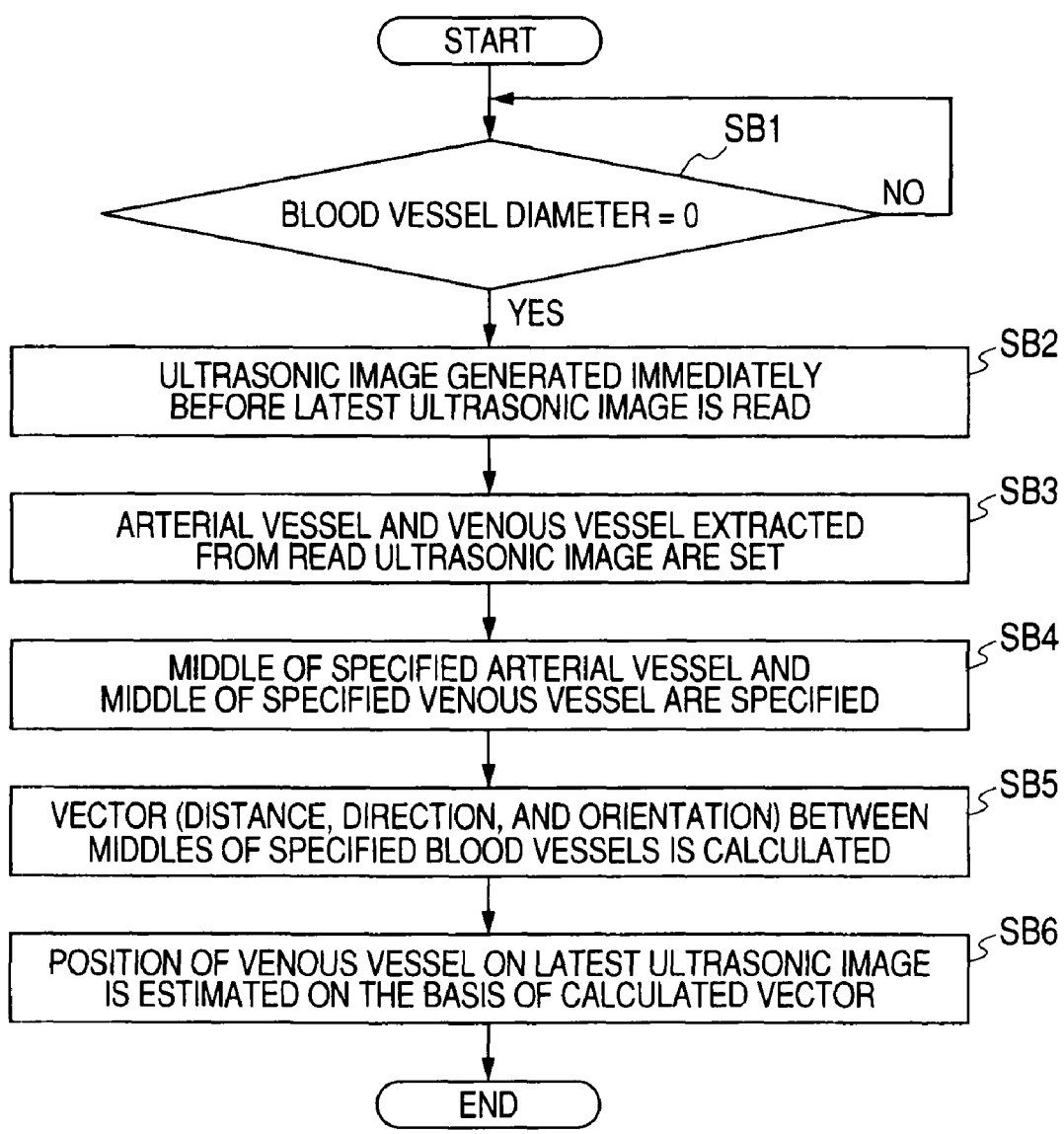
FIG. 7 is a view illustrating the flow of blood vessel estimation processing performed by a blood vessel position estimating unit shown in FIG. 1.

Moreover, in step SA9, there is a case in which the blood vessel diameter of a venous vessel visualized on the newest ultrasonic image becomes 0 by pressure or the like. Since the venous vessel cannot be observed when the blood vessel diameter is 0, for example, a doctor misses the position of the venous vessel. In order to prevent the position of a venous vessel from missing, blood vessel position estimation processing is performed by the blood vessel position estimating unit 28. Hereinafter, a flow of the blood vessel position estimation processing will be described with reference to FIG. 7.

[Step SB1]

The control unit 38 waits for the blood vessel diameter of the venous vessel calculated in step SA9 to become 0. When the blood vessel diameter becomes 0, the control unit 38 makes the blood vessel position estimating unit 28 perform the blood vessel estimation processing.

[Step SB2]

The blood vessel position estimating unit 28 reads an ultrasonic image, which is generated immediately before a newest ultrasonic image in which the blood vessel diameter of the venous vessel is 0, from the storage unit 23. In addition, if the blood vessel diameter of the venous vessel in the ultrasonic image generated immediately before the newest ultrasonic image is also 0, the blood vessel position estimating unit 28 reads an ultrasonic image with a larger venous vessel than 0 from ultrasonic images generated in step SA6.

[Step SB3]

Figure 8:
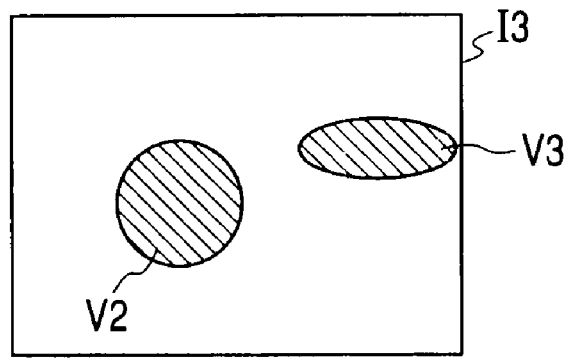
FIG. 8 is a view illustrating an ultrasonic image generated immediately before a newest ultrasonic image in order to explain step SB4 shown in FIG. 7.

First, the blood vessel position estimating unit 28 specifies an arterial vessel and a venous vessel, which are visualized on the ultrasonic image generated immediately before, on the basis of a Doppler signal generated due to a blood flow. FIG. 8 is a view illustrating an ultrasonic image 13 generated immediately before. As shown in FIG. 8, an arterial vessel V2 usually runs side by side with a venous vessel V3. In addition, the arterial vessel V2 does not deform even if the arterial vessel V2 is pressed by the probe 10. The blood flow speed of the arterial vessel V2 is faster than that of the venous vessel V3. Therefore, the blood vessel position estimating unit 28 can distinguish the arterial vessel V2 from the venous vessel V3 with a Doppler signal and can specify the arterial vessel V2.

[Step SB4]

The blood vessel position estimating unit 28 performs elliptical approximation of the arterial vessel V2 and the venous vessel V3, which are visualized on the ultrasonic image 13 generated immediately before, and specifies a center C2 of the arterial vessel V2 and a center C3 of the venous vessel V3.

[Step SB5]

Figure 9:
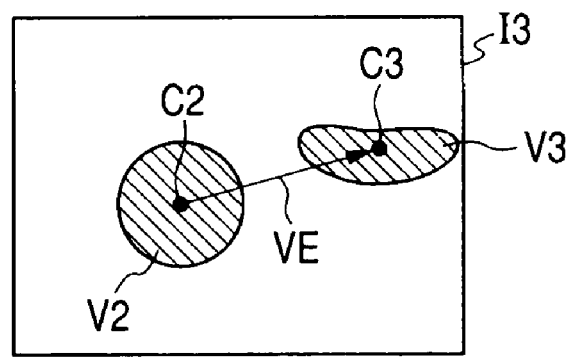
FIG. 9 is a view illustrating an ultrasonic image generated immediately before a newest ultrasonic image in order to explain step SB5 shown in FIG. 7.

The blood vessel position estimating unit 28 calculates a vector from the specified center C2 of the arterial vessel V2 to the specified center C3 of the venous vessel V3. FIG. 9 is a view illustrating a vector VE from the center C2 of the arterial vessel to the center C3 of the venous vessel. As shown in FIG. 9, calculating the vector VE means calculating distance, direction, and orientation between the center C2 of the arterial vessel V2 and the center C3 of the venous vessel V3.

[Step SB6]

Figure 10:
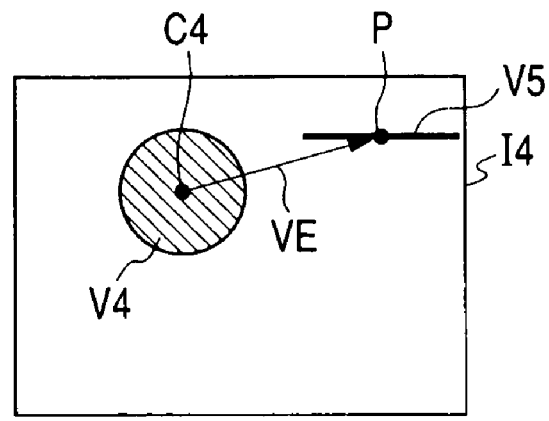
FIG. 10 is a view illustrating a newest ultrasonic image in order to explain step SB6 shown in FIG. 7.

The blood vessel position estimating unit 28 estimates the position of the venous vessel on the newest ultrasonic image on the basis of the calculated vector (distance, direction, and orientation) and the position of the center of the arterial vessel on the newest ultrasonic image. FIG. 10 is a view explaining step SB6. As shown in FIG. 10, the blood vessel position estimating unit 28 specifies the position of a center C4 of an arterial vessel V4 on a newest ultrasonic image 14. A method of specifying the position of the center C4 of the arterial vessel V4 is the same as that in step SB4. The blood vessel position estimating unit 28 sets a start point of the calculated vector VE at the position of the center C4 of the specified arterial vessel V4. The blood vessel position estimating unit 28 sets the position P, which is indicated by an end point of the set vector VE, as the position of the center of a venous vessel V5 on the newest ultrasonic image 14. By setting the position of the center of the venous vessel V5, the position of the venous vessel V5 can be estimated.

Thus, the processing for estimating the blood vessel position is completed. After the processing for estimating the blood vessel position is completed, processing in step SA10 is performed. Furthermore, in step SA11 immediately after the processing for estimating the blood vessel position is performed, the display image generating unit 30 generates a display image in which the position of the venous vessel estimated in step SB6 is indicated. A method of indication is to give an arrow to the estimated position, for example. As other methods of indication, a venous vessel may be highlighted by a color, be printed, or be displayed with the brightness changed.

In addition, even in the case where the blood vessel position estimation processing is not performed, the display image generating unit 30 may generate a display image in which the position of a venous vessel is indicated in the above methods (for example, an arrow) as long as the blood vessel diameter of a vein vessel is five pixels or less.

With the above configuration, it is possible to easily observe deformation of a blood vessel by automatically specifying the reference image and the maximum pressure image and displaying the images side by side, without observing an image generated in real time to observe deformation of a blood vessel caused by pressure like the related art. Furthermore, it becomes easier to observe the deformation of a blood vessel by calculating and displaying a stenosis rate of the blood vessel from the blood vessel diameter related to the reference image and the maximum pressure image. Moreover, by estimating the position of a vein on the basis of the positional relationship between an arterial vessel and a venous vessel in an ultrasonic image generated immediately before, the position of venous vessel is not missing even in the case when the venous vessel disappears completely by pressure of the probe 10. As a result, the existence of an intravascular thrombus or vascular stenosis and occlusion can be easily determined.

Second Embodiment

In a second embodiment, a pressure index value is a Doppler shift frequency changing according to the movement of a blood vessel or a change of a blood flow that is caused by pressing a tested body with the probe 10. Moreover, in the following description, a component having approximately the same function as in the first embodiment is denoted by the same reference numeral, and repeat of explanation will only be made as needed.

Figure 11:
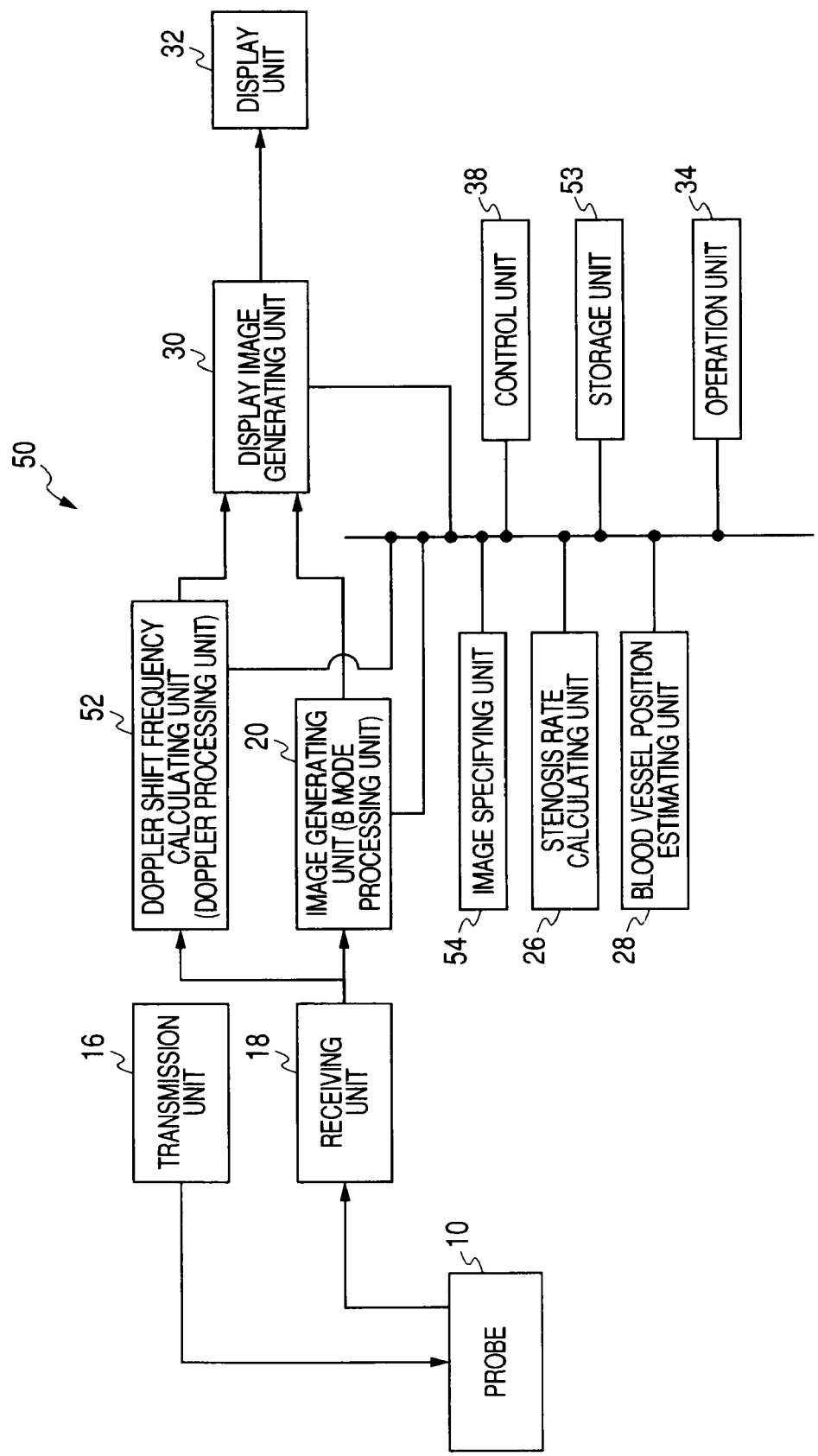
FIG. 11 is a view illustrating the configuration of an ultrasonic diagnostic apparatus according to a second embodiment of the invention.

FIG. 11 is a view illustrating the configuration of an ultrasonic diagnostic apparatus 50 according to a second embodiment of the invention. The ultrasonic diagnostic apparatus 50 includes a probe 10, a transmission unit 16, a receiving unit 18, an image generating unit (B-mode processing unit) 20, a Doppler shift frequency calculating unit (Doppler processing unit) 52, a storage unit 53, an image specifying unit 54, a stenosis rate calculating unit 26, a blood vessel position estimating unit 28, a display image generating unit 30, a display unit 32, an operation unit 34, and a control unit 38.

The Doppler shift frequency calculating unit 52 receives supply of an echo signal from the receiving unit 18 and calculates a signal shifted by the Doppler shift frequency by performing frequency analysis of the echo signal. The signal shifted by the Doppler shift frequency is called a Doppler signal. In particular, the Doppler signal generated due to the movement of a tissue in a tested body is called a tissue Doppler signal. The Doppler processing unit 52 calculates a movement speed, acceleration, and the like of a tissue, such as a blood vessel, in the tested body, on the basis of the calculated tissue Doppler signal. In addition, the Doppler processing unit 52 generates data of a Doppler image showing two-dimensional distribution on a predetermined section, such as a movement speed, acceleration, variance, or power of a tissue, such as a blood vessel, in the tested body.

The storage unit 53 stores data of an ultrasonic image and generation time thereof so as to be related to each other. The storage unit 53 stores data of a tissue Doppler signal and calculation time thereof so as to be related to each other. The storage unit 53 stores a tissue Doppler signal and an ultrasonic image, which is generated at approximately the same time as when the tissue Doppler signal is calculated, in a condition where the tissue Doppler signal and the ultrasonic image are related to each other. In addition, the storage unit 53 stores various kinds of data of a display image, a stenosis rate, and the like.

The image specifying unit 54 specifies a time at the maximum contact pressure from the tissue Doppler signal, which is calculated in real time by the Doppler processing unit 52, and specifies the ultrasonic image (maximum pressure image) stored in association with the time at the maximum contact pressure. Hereinafter, image specifying processing will be described with reference to FIG. 12.

Figure 12:
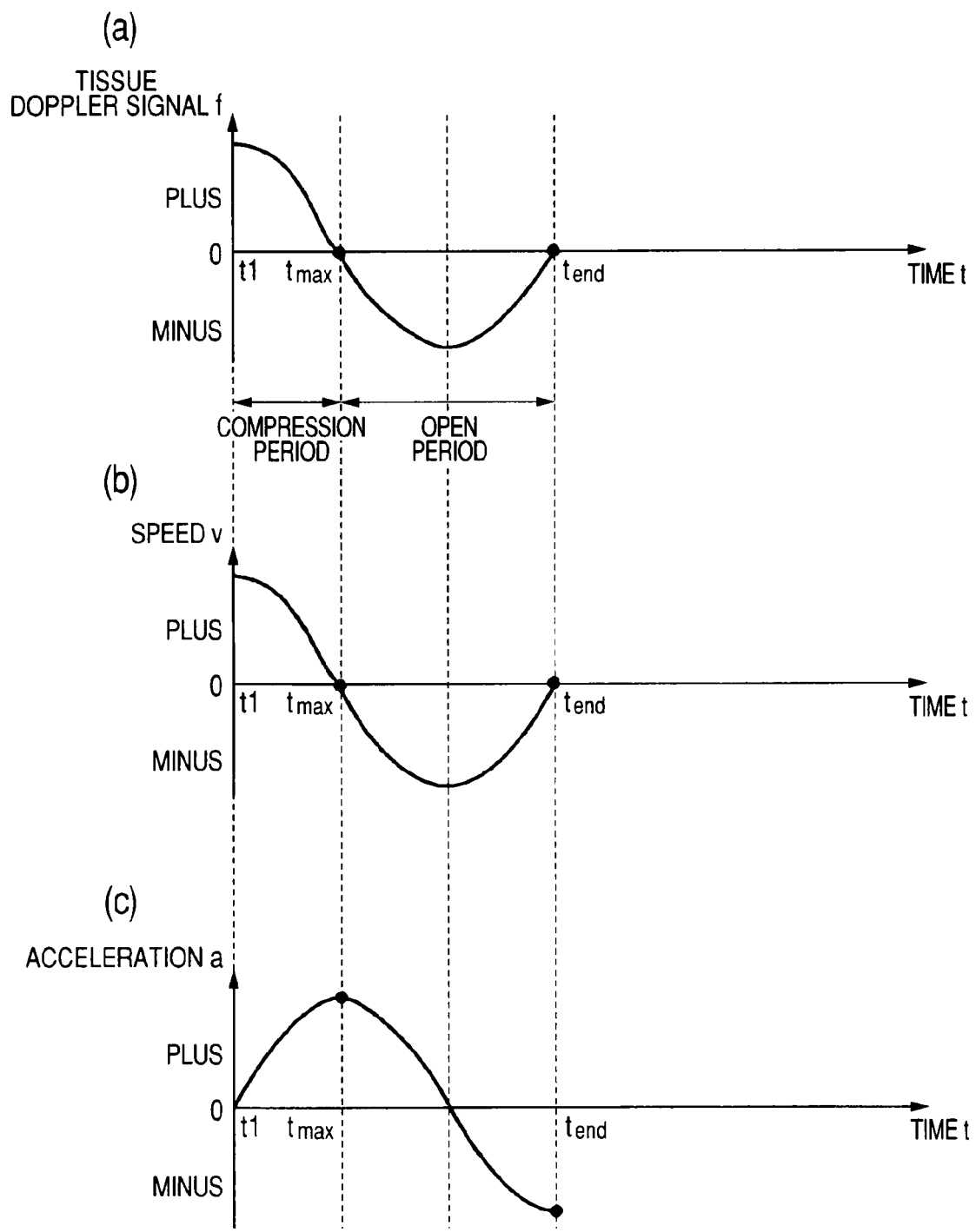
FIG. 12 is a view for explaining processing for specifying an image corresponding to a maximum contact pressure by means of an image specifying unit shown in FIG. 11.

(a) in FIG. 12 illustrates a temporal change of a tissue Doppler signal (frequency), (b) in FIG. 12 illustrates a temporal change of a velocity calculated from the tissue Doppler signal, and (c) in FIG. 12 illustrates a temporal change of acceleration calculated from the tissue Doppler signal. In addition, t1 is a time when the stenosis rate calculating button is pressed.

As shown at (a), (b), and (c) in FIG. 12, a pressure period can be estimated when components, which come closer to the probe 10, among tissue Doppler signal components of the entire ultrasonic image, are larger than components going away from the probe 10 and an open period can be estimated when the components coming closer to the probe 10 is smaller than the components going away from the probe 10. It can be estimated that a time $t_{max}$ at the true maximum contact pressure $p_{max}$ is a time when the velocity changes from plus to zero, that is, a time when the acceleration reaches a maximum value. Therefore, it can be estimated that a time when the tissue Doppler signal changes from plus to 0 is a true maximum contact pressure $t_{max}$. On the basis of such a theory, the image specifying unit 54 specifies the time when the tissue Doppler signal changes from plus to 0 from the tissue Doppler signal calculated in real time by the Doppler shift frequency calculating unit 52 and specifies an ultrasonic image, which is generated at approximately the same time as the specified time, as a true maximum pressure image.

Figure 13:
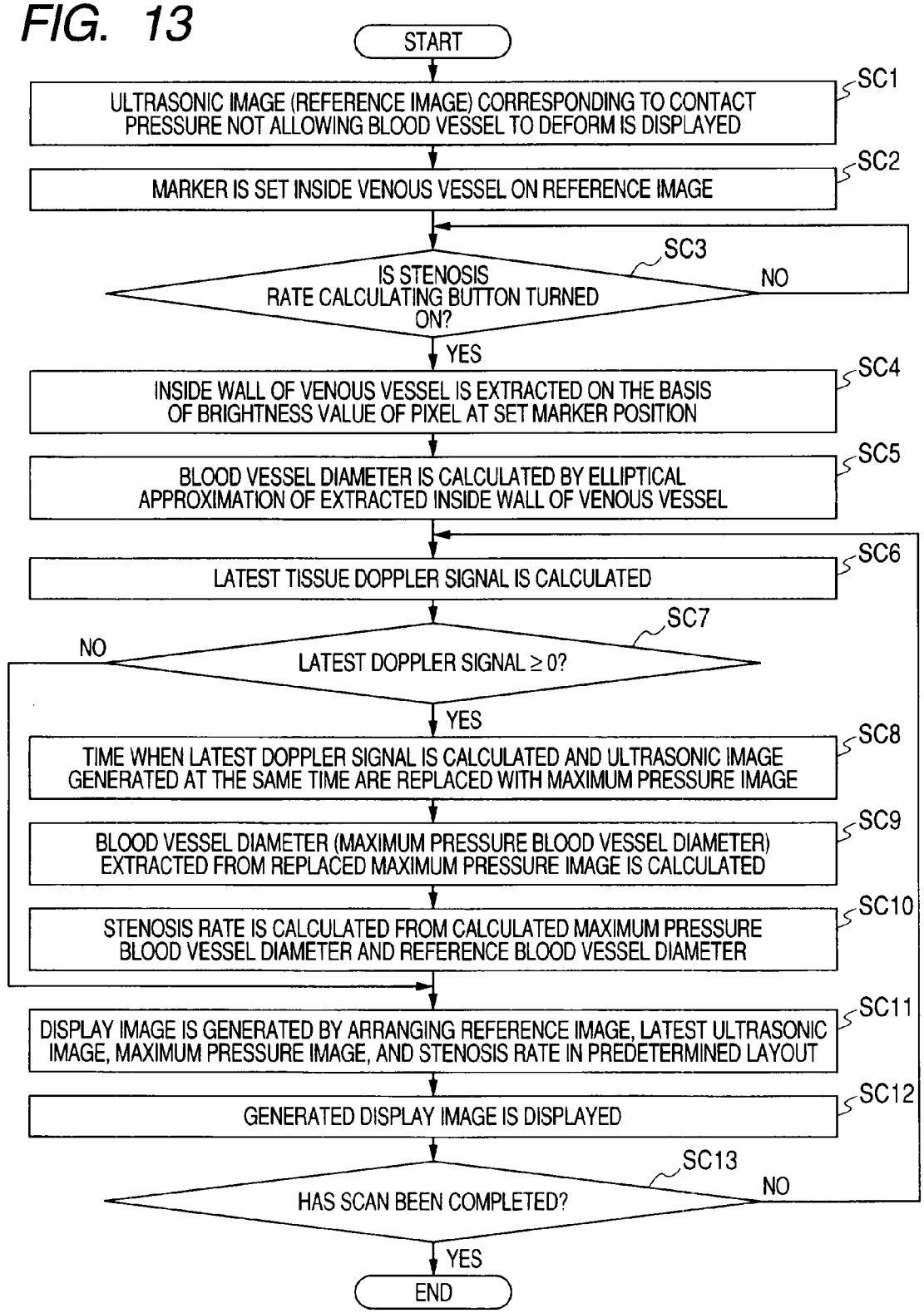
FIG. 13 is a view illustrating the flow of processing, which is performed under the control of a control unit shown in FIG. 11, in the second embodiment.

Hereinafter, a flow of an operation of the control unit 38 in the second embodiment will be described with reference to FIG. 13. In addition, the same processing as in the first embodiment will be briefly described.

[Step SC1]

First, an operator presses the probe 10 against a tested body with the reference contact pressure and presses the scan start button provided in the operation unit 34. When the scan start button is pressed, the control unit 38 generates a reference image by performing scan in a condition of the reference contact pressure and displays the generated reference image on the display unit 32.

[Step SC2]

The control unit 38 sets a marker inside a venous vessel on the reference image.

[Step SC3]

The control unit 38 waits for the operator to request processing for calculating a stenosis rate. The control unit 38 starts stenosis rate calculation processing when the operator presses the stenosis rate calculating button provided in the operation unit 34.

[Step SC4]

The stenosis rate calculating unit 26 extracts an inner wall of a venous vessel on the basis of a brightness value of a pixel at the position of the marker set in step SC2.

[Step SC5]

The stenosis rate calculating unit 26 performs elliptical approximation of the inner wall of the venous vessel extracted in step SC4 and calculates the reference blood vessel diameter.

[Step SC6]

When the reference blood vessel diameter is calculated in step SC5, the operator starts to press the tested body with the ultrasonic probe 10. While pressing the tested body, the control unit 38 scans the tested body through the probe 10 and generates data of an ultrasonic image in real time. In addition, a tissue Doppler signal is also calculated in real time. The calculated tissue Doppler signal changes according to the strength of the operator's pressure. By this scan, data of a newest ultrasonic image is generated and a newest contact pressure is calculated. The newest ultrasonic image generated is stored in the storage unit 23 so as to be related to the elapsed time from time t1, for example. In addition, the calculated newest tissue Doppler signal is also stored in the storage unit 23 so as to be related to the elapsed time from time t1.

[Step SC7]

When the tissue Doppler signal is calculated in step SC6, the control unit 38 makes the image specifying unit 54 perform image specifying processing. The image specifying unit 54 determines whether or not the newest tissue Doppler signal is equal to or larger than zero. When it is determined that the newest tissue Doppler signal is equal to or larger than zero, the image specifying unit 54 proceeds to step SC8. When it is determined that the newest tissue Doppler signal is smaller than zero, the image specifying unit 54 proceeds to step SC11. Since the tissue Doppler signal is equal to or larger than zero in the pressure period, the image specifying unit 54 proceeds from step SC7 to step SC8. Since the newest tissue Doppler signal is smaller than zero in the open period, the image specifying unit 54 proceeds from step SC7 to step SC11.

[Step SC8]

When it is determined that the tissue Doppler signal is equal to or larger than zero in step SC7, the image specifying unit 24 sets the newest Doppler signal as a Doppler signal at the maximum pressure, specifies an ultrasonic image generated at approximately the same time as when the Doppler signal at the maximum pressure is calculated, and replaces the specified ultrasonic image with a maximum pressure image. It is assumed that the maximum pressure image is updated each time during the pressure period.

[Step SC9]

The stenosis rate calculating unit 26 calculates the blood vessel diameter (maximum pressure vessel diameter) related to the maximum pressure image updated in step SC8.

[Step SC10]

The stenosis rate calculating unit 26 calculates a stenosis rate from the reference blood vessel diameter calculated in step SC5 and the maximum pressure vessel diameter calculated in step SC9.

[Step SC11]

The display image generating unit 30 generates a display image by arranging the reference image, the newest ultrasonic image, the maximum pressure image, and the stenosis rate in a predetermined layout.

[Step SC12]

The control unit 38 displays the generated display image on the display unit 32.

[Step SC13]

Steps SC6 to SC12 are repeated until the scan stop button provided in the operation unit 34 is pressed by the operator. The control unit 38 ends the scan when the scan stop button is pressed.

With the above configuration, also in the ultrasonic diagnostic apparatus 50 not including a pressure sensor, it is possible to automatically specify the maximum pressure image on the basis of a tissue Doppler signal and to easily observe deformation of a blood vessel by displaying the maximum pressure image and the reference image side by side.

In addition, blood vessel position estimation processing of the blood vessel position estimating unit 28 may also be performed in the second embodiment by using the same method as in the first embodiment.

MODIFIED EXAMPLES

In the first and second embodiments, examples using an ultrasonic image (B-mode image) on a two-dimensional tomographic plane have been explained. However, the invention does not need to be limited thereto but may also be applied to an ultrasonic image generated from volume data that is three-dimensional data. The ultrasonic image generated from volume data is assumed to be called a 3D image. In description of the following modified examples, a pressure index value is assumed to be a contact pressure in the same manner as in the first embodiment. However, in the modified examples, the pressure index value may also be a Doppler shift frequency.

The ultrasonic diagnostic apparatus 1 in the modified example repeatedly scans a three-dimensional region of a tested body with an ultrasonic wave by using a probe 10'.

An image generating unit 20' reconstructs volume data on the basis of brightness data from the probe 10' and generates data of the 3D image related to a predetermined section by performing, for example, volume rendering on the volume data. In addition, in the case when a venous vessel is not visualized on the 3D image, the image generating unit 20' automatically traces the venous vessel included in volume data and generates data of the 3D image in which the venous vessel is visualized. More specifically, in the case when a venous vessel is not visualized on the 3D image, the image generating unit 20' specifies a venous vessel in the volume data through a correlation matching method, for example, and generates a 3D image, in which the specified venous vessel is visualized, from the volume data. The correlation matching method will be described later.

A storage unit 23' stores data of the 3D image and generation time thereof so as to be related to each other. The storage unit 23' stores data of a contact pressure and generation time thereof so as to be related to each other. In addition, the storage unit 23' stores data of a contact pressure with data of the 3D image, which is generated at approximately the same time as the contact pressure is calculated, in a condition where the data is related to each other. In addition, the storage unit 23' stores various kinds of data of a display image, a stenosis rate, and the like.

For example, an image specifying unit 24' specifies a maximum contact pressure from the contact pressure repeatedly calculated by the contact pressure calculating unit 14 and specifies a 3D image related with the maximum contact pressure.

Hereinafter, a flow of processing of the ultrasonic diagnostic apparatus in the modified example will be described. Since the basic flow in the modified example is almost the same as that in the first embodiment, the flow will be described with reference to FIG. 3. In addition, when referring to FIG. 3, it is assumed that 'step SA' is 'step SD' and an 'ultrasonic image' is a '3D image'.

[Step SD1]

Figure 14A:
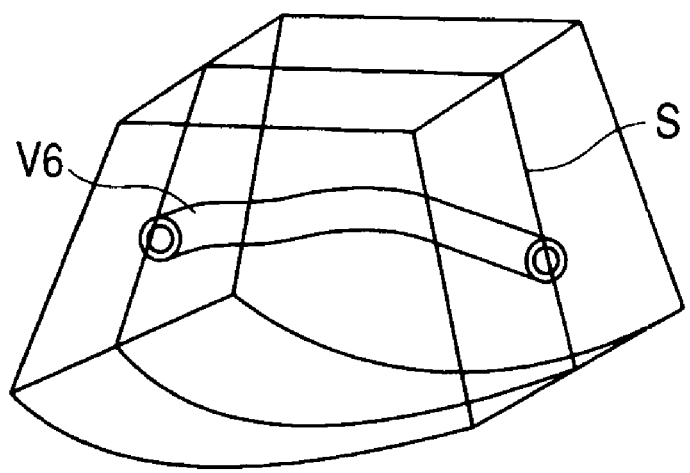
FIGS. 14A and 14B are views illustrating volume data and a 3D image in modified examples of the first and second embodiments.
Figure 14B:
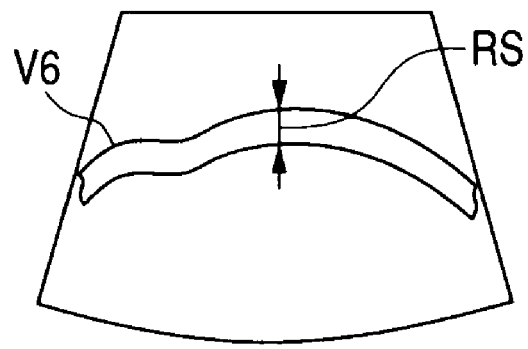

First, an operator presses the probe 10' against a tested body with the reference contact pressure and presses the scan start button provided in the operation unit 34. When the scan start button is pressed, the control unit 38 generates volume data by performing 3D scan in a condition of the reference contact pressure and displays a 3D image of an arbitrary 3D section on the display unit 32. FIGS. 14A and 14B are views illustrating volume data and a 3D image. Volume data corresponding to a reference contact pressure shown in FIG. 14A is generated by performing 3D scan of a tested body under the reference contact pressure. The generated volume data includes a region of a venous vessel V6. In addition, an operator specifies a 3D image on a section S where the venous vessel is displayed well through the operation unit 34. FIG. 14B is a view illustrating a specified 3D image.

[Step SD2]

The control unit 38 causes an operator to set a marker inside a venous vessel on the 3D image, which is specified in step SD1, through the operation unit 34.

[Step SD3]

The control unit 38 waits for the operator to request processing for calculating a stenosis rate. The control unit 38 makes the stenosis rate calculating unit 26 start stenosis rate calculation processing when the operator presses the stenosis rate calculating button provided in the operation unit 34.

[Step SD4]

The stenosis rate calculating unit 26 extracts an inner wall of a venous vessel on the basis of a brightness value of a pixel at the position of the marker set in step SD2.

[Step SD5]

The stenosis rate calculating unit 26 performs elliptical approximation of the inner wall of the venous vessel extracted in step SD4 and calculates a reference blood vessel diameter RS.

[Step SD6]

When the reference blood vessel diameter is calculated in step SD5, the operator starts to press the tested body with the probe 10' and the control unit 38 performs 3D scan. The control unit 38 generates data of a 3D image related to the same sectional position (coordinates) as the 3D image displayed in step SD1 in real time on the basis of an output from probe 10'. In addition, a contact pressure is also calculated in real time during the 3D scan.

When a venous vessel moves or the sectional position shifts due to pressing the tested body, the venous vessel may not be visualized in the 3D image generated in step SD6. In this case, the control unit 38 makes the image generating unit 20' automatically trace the venous vessel. There are various kinds of tracing methods. For example, there is a correlation matching method. Hereinafter, the correlation matching method will be briefly described.

Volume data at the current moment and volume data generated immediately before the volume data at the current moment are considered. A region of a venous vessel in the volume data generated immediately before is assumed to be called a reference region. In addition, a region which is cut from a proper position of the current volume data and which has the same shape and volume as the reference region is assumed to be called a comparison region.

First, the image generating unit 20' calculates the average, variance, and covariance in each of the reference region and the comparison region and calculates a coefficient of correlation between the reference region and the comparison region on the basis of the calculated average, variance, and covariance. A maximum value of the coefficient of correlation is 1 and a minimum value thereof is −1. It means that the reference region and the comparison region are similar as the coefficient of correlation is close to the maximum value 1. The image generating unit 20' calculates a coefficient of correlation while changing the position of the comparison region and considers the comparison region, in which a coefficient of correlation becomes largest, as a region corresponding to the reference region. The image generating unit 20' calculates the amount of positional deviation between the reference region and the region corresponding to the reference region and shifts the sectional position by the amount of positional deviation. In addition, the image generating unit 20' generates data of a 3D image related to the sectional position after shifting on the basis of volume data.

[Step SD7]

When the contact pressure is calculated in step SD6, the control unit 38 makes the image specifying unit 24' perform image specifying processing. In the image specifying processing, the image specifying unit 24' compares a value of a newest contact pressure with a value of a maximum contact pressure. When it is determined that the newest contact pressure is larger than the maximum contact pressure, the image specifying unit 24' proceeds to step SD8. When it is determined that the newest contact pressure is smaller than the maximum contact pressure, the image specifying unit 24' proceeds to step SD11.

[Step SD8]

When it is determined that the newest contact pressure is larger than the maximum contact pressure in step SD7, the image specifying unit 24' sets the newest contact pressure to the maximum contact pressure. When the maximum contact pressure is set, the image specifying unit 24' replaces the 3D image, which is generated at approximately the same time as when the maximum contact pressure is calculated, with a maximum pressure image. It is assumed that the maximum pressure image is updated each time during the pressure period.

[Step SD9]

The stenosis rate calculating unit 26 calculates the blood vessel diameter (maximum pressure vessel diameter) in the maximum pressure image updated in step SD8.

[Step SD10]

The stenosis rate calculating unit 26 calculates a stenosis rate from the reference blood vessel diameter calculated in step SD5 and the maximum pressure vessel diameter calculated in step SD9.

[Step SD11]

The display image generating unit 30 generates a display image by arranging the reference image generated in step SD1, the 3D image generated in step SD6, the maximum pressure image updated in step SD8, and the stenosis rate calculated in step SD10 in a predetermined layout.

[Step SD12]

The control unit 38 causes the display unit 32 to display the image generated in step SD11.

[Step SD13]

Steps SD6 to SD12 are repeated until the scan stop button provided in the operation unit 34 is pressed by the operator. The control unit 38 ends the scan when the scan stop button is pressed.

According to the modified example, when observing a venous vessel in a 3D image, it is possible to solve difficulty in observing a venous vessel caused in the case where the sectional position shifts or the venous vessel moves due to pressing a tested body.

In addition, the invention is not limited to the embodiments described above but may be embodied in practice by modifying constituent components without departing from the scope and spirit of the invention. In addition, various kinds of inventions may be realized by proper combination of the plurality of constituent components disclosed in the embodiments described above. For example, some constituent components may be removed from all the constituent components shown in the embodiments. Moreover, constituent components in different embodiments may be appropriately combined.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An ultrasonic diagnostic apparatus that repeatedly scans a tested body with an ultrasonic wave by using a probe, comprising:
   a generation unit configured to generate B-mode images associated with a blood vessel based on an output of the probe;
   a first calculation unit configured to repeatedly calculate first index values related to pressure of the probe against the tested body based on a physical quantity changing with the strength of the pressure;
   a specifying unit configured to specify a first B-mode image and a second B-mode image among the generated B-mode images, the first B-mode image corresponding to a maximum value of the calculated first index values, the second B-mode image corresponding to a non-maximum value of the calculated first index values; and
   a display unit configured to display the specified first B-mode image and second B-mode image side by side.

2. The ultrasonic diagnostic apparatus according to claim 1, further comprising:
   a storage unit configured to store the first index values and the B-mode images, each of the first index values being related to a B-mode image among the B-mode images, the related B-mode image being generated at a time approximating a time when a corresponding first index value is calculated,
   wherein the specifying unit sets a B-mode image related to the maximum index value on the storage unit to the first B-mode image.

3. The ultrasonic diagnostic apparatus according to claim 2,
   wherein the specifying unit sets a minimum value of the first index values to the non-maximum value and sets a B-mode image related to the minimum value on the storage unit to the second B-mode image.

4. The ultrasonic diagnostic apparatus according to claim 2,
   wherein the specifying unit compares a newest first index value of the first index values with the maximum value when the newest first index value is calculated and sets a B-mode image related to the newest first index value to the first B-mode image when the newest first index value is larger than the maximum value.

5. The ultrasonic diagnostic apparatus according to claim 1, further comprising:
   a second calculation unit configured to calculate a second index value related to deformation of the blood vessel based on a difference between the shape of the blood vessel visualized on the first B-mode image and the shape of the blood vessel visualized on the second B-mode image.

6. The ultrasonic diagnostic apparatus according to claim 1,
   wherein
   a second calculation unit calculates a stenosis rate of the blood vessel as a second index value based on a first blood vessel diameter of the blood vessel visualized on the first B-mode image and a second blood vessel diameter of the blood vessel visualized on the second B-mode image.

7. The ultrasonic diagnostic apparatus according to claim 6, further comprising:
   an estimation unit configured to estimate the position of the blood vessel on the first B-mode image from a positional relationship between the position of the blood vessel on the second B-mode image and the position of a reference portion on the second B-mode image,
   wherein a relative positional relationship between the reference portion and the blood vessel remains unchanged and the display unit indicates the estimated position on the displayed first B-mode image.

8. The ultrasonic diagnostic apparatus according to claim 6,
   wherein the display unit displays the calculated stenosis rate together with the first B-mode image and the second B-mode image.

9. The ultrasonic diagnostic apparatus according to claim 1, further comprising:
   a pressure sensor configured to generate an electric signal changing with the strength of the pressure that is the physical quantity, wherein the first calculation unit calculates the contact pressure values as the first index values based on the generated electric signal.

10. The ultrasonic diagnostic apparatus according to claim 1,
    wherein the first calculation unit calculates a Doppler shift frequency as the first index values based on the output of the probe that is the physical quantity, the Doppler shift frequency being due to a specific portion moving within the tested body by the pressure.

11. The ultrasonic diagnostic apparatus according to claim 1,
    wherein the probe transmits an ultrasonic wave to a three-dimensional region of the tested body and receives an ultrasonic wave reflected in the three-dimensional region, and
    the generation unit generates volume data based on the output of the probe and generates a B-mode image associated with a predetermined section based on the generated volume data.

12. The ultrasonic diagnostic apparatus according to claim 11, wherein the volume data includes a first volume data and a second volume data generated before the first volume data,
    the B-mode image associated with the predetermined section includes a comparison B-mode image associated with the predetermined section based on the first volume data, and a reference B-mode image associated with the predetermined section based on the second volume data, and
    the generation unit specifies, when a specific portion is not visualized on a the comparison B-mode image but the specific portion is visualized on a the reference B-mode image, the position of the specific portion included in the first volume data by tracing the specific portion visualized on the reference B-mode image and generates a B-mode image associated with a section crossing the specified specific portion from the first volume data.

13. An image display method of an ultrasonic diagnostic apparatus that repeatedly scans a tested body with an ultrasonic wave by using a probe, comprising:
    generating B mode images associated with a blood vessel based on an output of the probe repeatedly;
    calculating first index values related to pressure of the probe against the tested body based on a physical quantity changing with the strength of the pressure repeatedly;

specifying a first B-mode image and second B-mode image among the generated B-mode images, the first B-mode image corresponding to a maximum value of the calculated first index values, the second B-mode image corresponding to a non-maximum value of the calculated first index values; and displaying the specified first B-mode image and second B-mode image side by side.

14. The image display method of an ultrasonic diagnostic apparatus according to claim 13, wherein a B-mode image related to the maximum value is set to the first B-mode image.

15. The image display method of an ultrasonic diagnostic apparatus according to claim 14, wherein a minimum value of the first index values is set to a non-maximum value and a B-mode image related to the non-maximum value is set to the second B-mode image.

16. The image display method of an ultrasonic diagnostic apparatus according to claim 14, wherein a newest first index value of the first index values is compared with the maximum value when the newest first index value is calculated and a B-mode image related to the newest first index value is set to the first B-mode image when the newest first index value is larger than the maximum value.

17. The image display method of an ultrasonic diagnostic apparatus according to claim 13, wherein a second index value related to deformation of the blood vessel based on a difference between the shape of the blood vessel visualized on the first B-mode image and the shape of the blood vessel visualized on the second B-mode image is calculated.

18. The image display method of an ultrasonic diagnostic apparatus according to claim 13, wherein a stenosis rate of the blood vessel is calculated as a second index value based on a first blood vessel diameter of the blood vessel visualized on the first B-mode image and a second blood vessel diameter of the blood vessel visualized on the second B-mode image.

19. The image display method of an ultrasonic diagnostic apparatus according to claim 18, wherein the position of the blood vessel on the first B-mode image is estimated from a positional relationship between the position of the blood vessel on the second B-mode image and the position of a reference portion on the second B-mode image, a relative positional relationship between the reference portion and the blood vessel remains unchanged, and the estimated position is indicated on the displayed first B-mode image.

20. The image display method of an ultrasonic diagnostic apparatus according to claim 18, wherein the calculated stenosis rate is displayed together with the first B-mode image and second B-mode image.

21. The image display method of an ultrasonic diagnostic apparatus according to claim 13, wherein contact pressure values between the probe and the tested body are calculated as the first index values related to the pressure based on an electric signal generated by a pressure sensor, the electric signal being the physical quantity changing with the strength of the pressure.

22. The image display method of an ultrasonic diagnostic apparatus according to claim 13, wherein a Doppler shift frequency, which is generated due to a specific portion moving within the tested body by the pressure, is calculated as the first index values based on the output of the probe that is the physical quantity.

23. The image display method of an ultrasonic diagnostic apparatus according to claim 13, wherein a three-dimensional region of the tested body is scanned with an ultrasonic wave by using the probe, volume data is generated based on the output of the probe, and a B-mode image associated with a predetermined section is generated based on the generated volume data.

24. The image display method of an ultrasonic diagnostic apparatus according to claim 23, wherein the volume data includes a first volume data and a second volume data generated before the first volume data, the B-mode image associated with the predetermined section includes a comparison B-mode image associated with the predetermined section based on the first volume data, and a reference B-mode image associated with the predetermined section based on the second volume data, the position of a specific portion included in the first volume data is specified, when the specific portion is not visualized on the comparison image but the specific portion is visualized on a the reference image, by tracing the specific portion visualized on the reference image and a B-mode image associated with a section crossing the specified specific portion from the first volume data.

* * * * *